United States Patent [19]

Yamazaki et al.

[11] 4,120,853

[45] Oct. 17, 1978

[54] ESTERIFICATION OF CARBOXYLIC ACIDS BY CONTACT WITH A PHOSPHONIUM SALT

[75] Inventors: Noboru Yamazaki; Fukuji Higashi, both of Tokyo, Japan

[73] Assignee: Sumitomo Chemical Company, Limited, Osaka, Japan

[21] Appl. No.: 815,242

[22] Filed: Jul. 13, 1977

Related U.S. Application Data

[60] Division of Ser. No. 688,289, May 20, 1976, which is a division of Ser. No. 475,877, Jun. 3, 1974, Pat. No. 3,974,219, which is a continuation-in-part of Ser. No. 305,256, Nov. 10, 1972, abandoned.

[30] Foreign Application Priority Data

Nov. 22, 1971 [JP] Japan .................................. 46-93872
Feb. 19, 1972 [JP] Japan .................................. 47-17355

[51] Int. Cl.² ............................................. C07C 103/52
[52] U.S. Cl. .............................. 260/112.5 R; 560/19; 560/24; 560/38; 560/157; 560/169
[58] Field of Search ................... 260/112.5 R; 560/19, 560/24, 38, 157, 169

[56] References Cited

U.S. PATENT DOCUMENTS 2,938,915  5/1960  Schwyzer et al. .................... 260/389
3,907,855  9/1975  Yamazak et al. ................. 260/455 R

OTHER PUBLICATIONS

Gawne, G., et al., J. Amer. Chem. Soc. 1969, 91(20), 5669–5671.

*Primary Examiner*—Delbert R. Phillips
*Assistant Examiner*—Blondel Hazel
*Attorney, Agent, or Firm*—Stevens, Davis, Miller & Mosher

[57] ABSTRACT

The amidation and esterification of carboxylic acids with amines and hydroxyl group-containing compounds, respectively, are effected without incurring the drawbacks of reaction equilibrium by the reaction of the reactants, one of which has been activated in the reactive group by contact with a phosphonium salt obtained by reacting a phosphorous ester or phosphorous monoester salt with an organic base such as pyridine and an oxidizing agent such as halogens and mono or divalent mercury halide or acetate. The amidation can be applied to the preparation of peptides by the reaction of amino acids and/or peptides in which one of the reactive groups have been protected.

4 Claims, No Drawings

ESTERIFICATION OF CARBOXYLIC ACIDS BY CONTACT WITH A PHOSPHONIUM SALT

CROSS REFERENCE TO THE RELATED APPLICATION

This is a Division of application Ser. No. 688,289 filed May 20, 1976 which in turn is a division of application Ser. No. 475,877, filed June 3, 1974, now U.S. Pat. No. 3,974,219, which in turn is a continuation-in-part of application Ser. No. 305,256, filed Nov. 10, 1972, now abandoned.

This invention relates to a process for the activation of carboxyl, amino, hydroxyl or mercapto group-containing compounds. More particularly, the invention pertains to a process for activating the carboxyl, amino, hydroxyl or mercapto groups of the said compounds by use of reactive specific phosphonium salts. The invention is further concerned with a process for conducting amidation, peptidation or esterification reaction characterized by using activated carboxyl, amino, hydroxyl or mercapto group-containing compounds.

Heretofore, the amidation of carboxylic acids has been effected according to a process in which the acids are heated with amines and dehydrated in the presence or absence of a catalyst. The reaction according to this process, however, is an equilibrium reaction, and hence has brought about various drawbacks.

Peptide formation reactions have been carried out according to various processes. These processes, however, have had the drawbacks that carboxyl or hydroxyl groups which are ordinarily present in the side chains should be previously protected with certain groups, and the protective groups should be removed after the reaction. Even in the case of processes in which no protective groups are required to be used, there have been such drawbacks that the processes are low in selectivity and yield.

The synthesis of esters has typically been carried out according to a process in which organic acids are reacted with alcohols in the presence of an acid catalyst. This process, however, is not suitable for application to organic acids and alcohols which display great steric hindrance and, in addition, has had the drawback that the reaction does not proceeds quantitatively since the reaction system is an equilibrium system. Further, the said process is not applicable to the esterification of phenols. In case the esterification process using an acid catalyst is not effective, there has been adopted a process in which other activated compounds, for example, acid chlorides, acid anhydrides or diazomethane are used. However, the synthesis of these activated compounds is not always easy, and actually the process is not employed, in general, except in the case of acetic acid.

For the production of active esters of amino acids, there is a mixed anhydride process in which a chlorocarbonic ester, for example, is treated with an amino acid whose amino group has been protected, but this process is not sufficient in selective alcoholysis and hence is not so favorable in yield. In addition, there are an acid chloride process and an oxidation-reduction process. These processes, however, are not economically advantageous since the starting materials used are not easily synthesizable and specific reagents are required to be used.

In consideration of such points as mentioned above, the present inventors made extensive studies to find that when the carboxyl, amino, hydroxyl or mercapto groups of compounds containing said groups are activated by use of reactive specific phosphonium salts, such condensation reactions as amidation, esterification or peptidation proceed under extremely mild conditions and can be easily practiced even in a system in which the reaction has taken place with difficulty hitherto. Based on the above finding, the inventors have accomplished the present invention. The amidation reaction according to the present invention is a non-equilibrium reaction, and proceeds substantially completely.

The specific phosphonium salts used in the present invention are phosphonium salts obtained by reacting phosphorous esters or phosphorous monoester salts with organic bases and oxidizing agents. Concrete examples of the phosphorous esters used in the above case include monomethyl, monoethyl, monoisopropyl, monophenyl, dimethyl, diethyl, diisopropyl, di-n-butyl, diphenyl, triethyl, triisopropyl and tributyl esters of phosphorous acid, and ammonium salts of said monoesters. In case the phosphorous monoesters are used in the presence of organic bases, the monoesters are placed in the form of salts of said organic bases. It is therefore needless to say that salts of the organic bases used in the aforesaid reaction are also included in the phosphorous monoester salts. Generally, the amounts of the esters are equal to or more than the amounts of the compounds to be activated. Preferable examples of the organic bases used in the aforesaid case are pyridine, 2-methylpyridine, 3-methylpyridine, 4-methylpyridine, 2,6-dimethylpyridine, triethylamine and the like tertiary amines. Among these, pyridine is particularly preferable. Examples of the oxidizing agents used in the aforesaid case are halogens, and monovalent or divalent mercury halides or acetates. Preferable oxidizing agents include bromine, iodine, mercurous chloride, mercuric chloride, mercuric bromide and mercuric acetate. The proportions of the oxidizing agents used are at least a half of equimolar, generally equimolar to the phosphorous esters.

The specific phosphonium salts used in the present invention are obtained by treating the aforesaid phosphorous esters or phosphorous monoester salts with oxidizing agents in the presence of organic bases. The organic bases act as acid acceptors and catalysts.

In case the organic base is liquid, it acts also as a solvent, so that the use of other reaction solvent is not essential. If desired, however, the reaction may be carried out in the presence of such an inert solvent as acetonitrile. In this case, the organic base is preferably present in a proportion of 4 equivalents or more based on the phosphorous esters used. The reaction temperature employed in the phosphonium salt formation reaction is in the range of from 30° to 200° C., preferably from 50° to 150° C., and is ordinarily the reflux temperature of the reaction mixture. If the temperature is lower than 30° C., the reaction rate is low, while if the temperature is higher than 200° C., side reactions are undesirably brought about.

The present invention is explained in more detail below with reference to the case where phosphorous monoalkyl ester, pyridine and mercuric chloride are used.

0.05 Mole of phosphorous monoalkyl ester is refluxed for 1 hour in 20 ml. of pyridine in the presence of 0.05 mole of mercuric chloride, whereby the system becomes turbid. Subsequently, the system is cooled to obtain a phosphonium salt as an ether insoluble substance. The thus obtained phosphonium salt is considered to have the following structure:

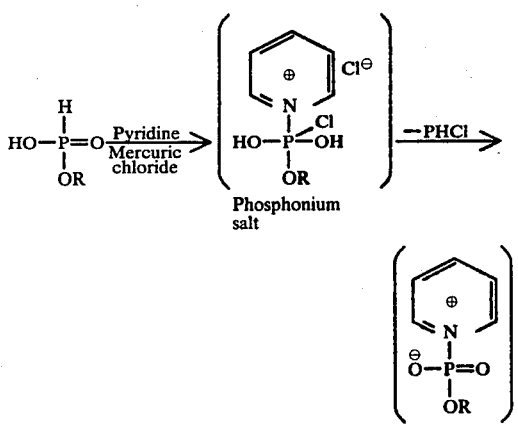

In the case of phosphorous dialkyl ester, the structure is considered to be as follows:

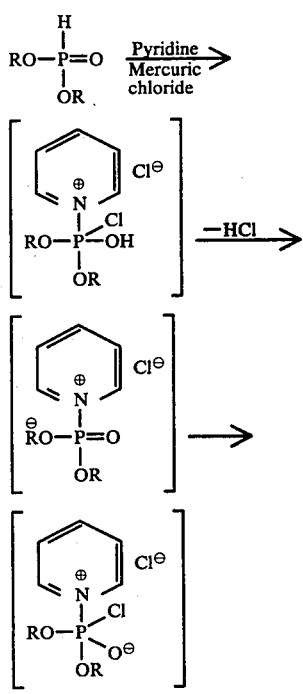

In the case of phosphorous trialkyl ester, the structure is considered to be as follows:

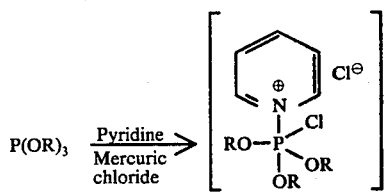

The present invention provides a process for activating a carboxyl, amino, hydroxyl, or mercapto group-containing compound by use of the reactive specific phosphonium salt obtained in the above-mentioned manner.

The present invention further provides a process for the amidation of a carboxylic acid, characterized in that the carboxyl group of a carboxylic acid or amino group of an amine is activated, and the activated acid is reacted with an amine in case the carboxyl group containing compound has been activated, or the activated amine is reacted with a carboxylic acid in case the amino group containing compound has been activated; a process for peptide formation, characterized in that the carbonyl or amino group of an amino acid having a protected amino or carbonyl group respectively is activated, and the activated compound is reacted with an amino acid; a process for the esterification of a carboxylic acid, characterized in that the carboxyl group of a carboxylic acid or hydroxyl group of a hydroxyl group-containing compound is activated, and the activated acid is reacted with a hydroxyl group-containing compound in case the carboxyl group-containing compound has been activated, or the activated hydroxyl group-containing compound is reacted with a carboxyl group-containing compound in case the hydroxyl group-containing compound has been activated and a process for the production of an active ester of an amino acid having a protected amino group, characterized in that the carboxyl group of an amino acid having a protected amino group is activated, or the hydroxyl (mercapto) group of a hydroxyl (mercapto) group-containing compound is activated, and the activated compound is reacted with a hydroxyl (mercapto) group-containing compound in case the carboxyl group of the amino acid has been activated, or with an amino acid having a protected amino group in case the hydroxyl (mercapto) group of the hydroxyl (mercapto) group-containing compound has been activated.

In the present invention, the process for activating by use of a phosphonium salt, (a) the carboxyl group of a carboxylic acid represented by the formula,

wherein $R^1$ is an alkyl group having 1–30 carbon atoms, preferably 1–18 carbon atoms, a halogen-substituted alkyl group having 1–10 carbon atoms, preferably 1–6 carbon atoms, a cycloalkyl group having 3–8 carbon atoms, preferably 3–6 carbon atoms, a phenyl group, a lower alkyl (having 1–4 carbon atoms) substituted-phenyl group or a phenylalkyl group having 7–12 carbon atoms; (b) the amino group of an amine derivative represented by the formula,

wherein $R^2$ and $R^3$ are independently an alkyl group having 1–10 carbon atoms, preferably 1–4 carbon atoms, a cycloalkyl group having 3–8 carbon atoms, preferably 3–6 carbon atoms, a phenyl group, a lower alkyl or alkoxy (having 1–4 carbon atoms) substituted-phenyl group or a phenylalkyl group having 7–12 carbon atoms, and one of $R^2$ and $R^3$ may be a hydrogen atom; (c) the hydroxyl group of a hydroxyl group-containing compound or the mercapto group of a mercapto group-containing compound represented by the formula,

or

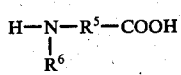 (III-b)

wherein $R^4$ is an alkyl group having 1–18 carbon atoms, preferably 1–6 carbon atoms, a cycloalkyl group having 3–8 carbon atoms, preferably 3–6 carbon atoms, a phenyl group, a naphthyl group, an aryl group having at least one substituent group selected from the group consisting of an alkyl group having 1–4 carbon atoms, a nitro group, a cyano group, a N,N-dimethylamino group and a methoxycarbonyl group, or a phenylalkyl group having 7–12 carbon atoms; or (d) the carboxyl group or the amino group of an amino acid represented by the formula,

 (IV)

wherein $R^5$ is an alkylene or alkylidene group having 1–30 carbon atoms which may have a substituent, such as a phenyl, salicyl, carbamoyl or carboxyl group, a cycloalkylene or cycloalkylidene group having 3–8 carbon atoms, a phenylene group, a group of the formula

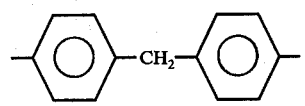

a group of the formula

or a group in which two or more groups selected from the group consisting of the above-mentioned aliphatic and aromatic hydrocarbon groups are bonded through —CONH— group; and $R^6$ is hydrogen or alkyl having 1–4 carbon atoms, may be carried out, for example, by reacting the said carboxyl, amino, hydroxyl or mercapto group-containing compound with a reaction mixture containing the phosphonium salt obtained in the aforesaid manner. The reaction temperature employed in the above-mentioned activation reaction is in the range of from 0° to 200° C., preferably from 20° to 150° C.

Examples of the carboxylic acid, which is to be activated with the phosphonium salt, include acetic acid, propionic acid, n-butyric acid, isobutyric acid, valeric acid, isovaleric acid, pivalic acid, caproic acid, caprylic acid, lauric acid, palmitic acid, stearic acid, trichloroacetic acid, trifluoroacetic acid, cyclohexanecarboxylic acid, benzoic acid, p-toluic acid, phenyl acetic acid and the like.

Specific examples of the amine derivative include methylamine, dimethylamine, ethylamine, methylethylamine, butylamine, cyclopropylamine, cyclohexylamine, N-methylcyclohexylamine, aniline, N-methylaniline, N-ethylaniline, toluidine, anisidine, phenetidine, xylidine, diphenylamine, benzylamine and the like.

Specific examples of the hydroxyl group-containing compound are methyl alcohol, ethyl alcohol, n-propyl alcohol, isopropyl, alcohol, n-butyl alcohol, sec-butyl alcohol, isobutyl alcohol, tert-butyl alcohol, hexyl alcohol, cyclopropanol, cyclopentanol, cyclohexanol, phenol, α-naphthol, β-naphthol, nitrophenol, dinitrophenol, cresol, xylenol, p-N,N-dimethylaminophenol, cyanophenol, methoxycarbonylphenol, benzyl alcohol, phenylethanol and the like and as the mercapto group-containing compound, methanethiol, ethanethiol, cyclohexanethiol, thiophenol and the like are exemplified.

Examples of the amino acid are glycine, glycylglycine, sarcosine, dimethylglycine, alanine, phenylalanine, α-aminobutyric acid, α-aminoisobutyric acid, valine, leucine, isoleucine, norleucine, glutamine, glutamic acid, α-aminoenanthic acid, α-aminocaprylic acid, α-aminopelargonic acid, α-aminocapric acid, α-aminoundecanoic acid, α-aminolauric acid, α-aminomyristic acid, α-aminostearic acid, α-aminoarachic acid, α-aminocerotic acid, α-aminomelissic acid, tyrosine, β-alanine, β-aminobutyric acid, β-aminoisobutyric acid, β-aminovaleric acid, γ-aminobutyric acid, γ-aminovaleric acid, δ-aminovaleric acid, ξ-aminocaproic acid, ω-aminoenanthic acid, ω-aminocaprylic acid, ω-aminopelargonic acid, ω-aminocapric acid, ω-aminoundecanoic acid, ω-aminotridecanoic acid, 4-aminocyclohexancarboxylic acid, p-aminobenzoic acid, p-(4-aminophenyl)benzoic acid, p-(4-aminobenzyl)benzoic acid and the like.

It is possible to adopt a process in which the phosphonium salt is separated from the phosphonium salt containing reaction mixture obtained in the aforesaid manner and is used to activate the said carboxylic acid, amine derivative, hydroxyl group-containing compound, mercapto group-containing compound and amino acid in which one of the reactive groups have been protected. In practice, however, the phosphonium salt is not required to be separated, and the above-mentioned process is economically disadvantageous since the separation of said salt is costly.

According to the present invention, an amide derivative of the formula,

 (V)

wherein $R^1$, $R^2$ and $R^3$ are as defined previously, is obtained by activating a carboxylic acid or an amine derivative with the thus obtained phosphonium salt and then reacting the activated compound with an amine of the formula (II) in case the carboxylic acid has been activated or with a carboxylic acid of the formula (I) in case the amine derivative has been activated; or a peptide is obtained by activating with the phosphonium salt an amino acid having a protected amino or carboxyl group and then reacting the activated amino acid with an amino acid having a protected carboxyl group or with a free amino acid in case the carboxyl group of the amino acid has been activated or with an amino acid having a protected amino group in case the amino group of the amino acid has been activated; or a compound of the formula, $$R^1COOR^4 \qquad (VI)$$

wherein $R^1$ and $R^4$ are as defined previously, is obtained by activating with the phosphonium salt a carboxylic acid or a hydroxyl (mercapto) group-containing compound and then reacting the activated compound with a hydroxyl or mercapto group-containing compound of the formula (III-a) or (III-b) in case the carboxylic acid has been activated or with a carboxylic acid of the formula (I) in case the hydroxyl or mercapto group-containing compound has been activated; or an active ester of an amino acid of the formula (IV) is obtained by activated with the phosphonium salt an amino acid having a protected amino group or a hydroxyl or mercapto group-containing compound of the formula (III-a) or (III-b) and then reacting the activated compound with a hydroxyl or mercapto group-containing compound in case the amino acid has been activated or with an amino acid having a protected amino group in case the hydroxyl or mercapto group-containing compound has been activated.

The compound activated with the phosphonium salt according to the present invention is a quite substance, difficult to isolate and the reaction mixture is ordinarily subjected as it is to amidation, peptidation or esterification reaction. Accordingly, the amidation reaction of a carboxylic acid is carried out, in general, by reacting the activation reaction mixture with an amine derivative in case the carboxylic acid has been activated or with a carboxylic acid in case the amine derivative has been activated. The same is the case with the peptidation and esterification reactions. The reaction temperature employed in the amidation, peptidation or esterification reaction is in the range of from 0° to 200° C., preferably from 20° to 150° C., and is ordinarily the reflux temperature of the reaction mixture.

In the present invention, the amino or carboxyl group of an amino acid may be protected according to any of the procedures which have heretofore been employed for the synthesis of peptides. For example, the carboxyl group is protected by adoption of such a procedure that the amino acid is converted to a lower alkyl ester, a benzyl ester or a salt thereof. Alternatively, the amino group is protected by adoption of such a procedure that the amino acid is acylated to protect said group with such a protective group as, for example, formyl, trifluoroacetyl, benzyloxycarbonyl, tertiary butoxycarbonyl or tertiary amyloxycarbonyl group. After completion of the peptide synthesis according to the present invention, the above-mentioned protective group can be released according to the ordinary procedure. For example, in case the amino protective group is a benzyloxycarbonyl group, the protective group can be released by catalytic reduction using a palladium catalyst in such a solvent as ethanol, dioxane, dioxane-water or dimethylformamide, and in case the amino protective group is a tertiary amyloxycarbonyl or the like group, the protective group can be released by treatment with trifluoroacetic acid or the like. Alternatively, in case the carboxyl protective group is an ester, the protective group can be released by treatment with trifluoroacetic acid, for example (Refer to Kirk-Othmer "Encyclopedia of Chemical Technology" second edition, vol. 2, page 170-171).

In the peptidation reaction, it is, of course, possible to repeat the aforesaid reaction to obtain a polypeptide.

The present invention is illustrated in more detail below with reference to examples, but it is needless to say that the invention is not limited to the examples.

EXAMPLE 1

A mixture of 5.5 g. (0.05 mole) of phosphorous monoethyl ester and 13.5 g. (0.05 mole) of mercuric chloride was heated under reflux (at about 115° C.) for 1 hour in 20 ml. of pyridine, whereby the reaction mixture became turbid to form a phosphonium salt. To the reaction mixture containing the phosphonium salt was added 3.0 g. (0.05 mole) of acetic acid, and heating was continued under reflux for 1 hour to activate the carboxyl group of said acetic acid. After completion of the activation reaction, the reaction mixture was incorporated with 5.2 g. (0.056 mole) of aniline and then reacted under reflux for 2 hours. The reaction liquid was concentrated and then dissolved in 40 ml. of methanol, and the resulting solution was neutralized under cooling with a concentrated aqueous ammonia solution and then poured into 200 ml. of acetone to precipitate an ammonium salt. The precipitated ammonium salt was separated by filtration, and the filtrate was concentrated. Subsequently, water was added to the residue to form a solid. This solid was sufficiently washed with water and then recrystallized from water to obtain 6.2 g. of acetanilide, yield 92% based on acetic acid used.

EXAMPLE 2

A mixture of 5.5 g. (0.05 mole) of phosphorous monoethyl ester, 13.5 g. (0.05 mole) of mercuric chloride and 3.0 g. (0.05 mole) of acetic acid was heated under reflux for 1 hour in 20 ml. of pyridine to carry out the formation of a phosphonium salt simultaneously with the activation of the carboxyl group of acetic acid. After completion of the reaction, the reaction mixture was incorporated with 5.2 g. (0.056 mole) of aniline and then reacted under reflux for 2 hours. Thereafter, the same after-treatment as in Example 1 was conducted to obtain 5.4 g. of acetanilide, yield 80% based on acetic acid used.

EXAMPLES 3-5

Example 1 was repeated, except that 0.05 mole of each of carboxylic acid shown in Table 1 was used in place of acetic acid. The results obtained were as set forth in Table 1.

Table 1

| Example | Carboxylic acid | Resulting anilide | Yeild (%) |
|---|---|---|---|
| 3 | Propionic acid | Propionanilide | 80 |
| 4 | n-Butyric acid | n-Butyranilide | 71 |
| 5 | Isobutyric acid | Isobutyranilide | 52 |

*based on carboxylic acid

EXAMPLES 6-11

Example 2 was repeated, except that 0.05 mole of each of carboxylic acids shown in Table 2 was used in place of acetic acid. The results obtained were as set forth in Table 2.

Table 2

| Example | Carboxylic acid | Resulting anilide | Yeild (%) |
|---|---|---|---|
| 6 | Propionic acid | Propionanilide | 70 |
| 7 | n-Butyric acid | n-Butyranilide | 59 |
| 8 | Benzoic acid | Benzanilide | 39 |
| 9 | Phenylacetic acid | Phenylacetanilide | 64 |
| 10 | Trifluoroacetic acid | Trifluoroacetanilide | 86 |

Table 2-continued

| Example | Carboxylic acid | Resulting anilide | Yeild (%) |
|---|---|---|---|
| 11 | Isobutyric acid | Isobutyranilide | 40 |

*based on carboxylic acid

EXAMPLES 12–14

Example 2 was repeated, except that 0.05 mole of each of phosphorous monoesters shown in Table 3 was used in place of phosphorous monoethyl ester. The results obtained were as set forth in Table 3.

Table 3

| Example | Phosphorous monoester | Acetanilide yield (%) |
|---|---|---|
| 12 | Phosphorous methyl ester | 74 |
| 13 | Phosphorous isopropyl ester | 74 |
| 14 | Phosphorous phenyl ester | 94 |

EXAMPLES 15–19

Example 1 was repeated, except that 0.05 mole of each of phosphorous diesters shown in Table 4 was used in place of phosphorous monoethyl ester. The results obtained were as set forth in Table 4.

Table 4

| Example | Phosphorous diester | Acetanilide yield (%) |
|---|---|---|
| 15 | Phosphorous dimethyl ester | 56 |
| 16 | Phosphorous diethyl ester | 77 |
| 17 | Phosphorous diisopropyl ester | 94 |
| 18 | Phosphorous di-n-butyl ester | 74 |
| 19 | Phosphorous diphenyl ester | 93 |

EXAMPLES 20–24

Example 1 was repeated, except that 0.05 mole of phosphorous diisopropyl ester was used in place of phosphorous monoethyl ester and 0.05 mole of each of carboxylic acids shown in Table 5 was used in place of acetic acid. The results obtained were as set forth in Table 5.

Table 5

| Example | Carboxylic acid | Resulting anilide | Yield* (%) |
|---|---|---|---|
| 20 | Propionic acid | Propionanilide | 94 |
| 21 | n-Butyric acid | n-Butyranilide | 98 |
| 22 | Isobutyric acid | Isobutyranilide | 97 |
| 23 | Pivalic acid | Pivalanilide | 70 |
| 24 | Benzoic acid | Benzanilide | 78 |

*based on carboxylic acid

EXAMPLES 25–27

Example 1 was repeated, except that 0.05 mole of each of phosphorous triesters shown in Table 6 was used in place of phosphorous monoethyl ester. The results obtained were as set forth in Table 6.

Table 6

| Example | Phosphorous triester | Acetanilide yield (%) |
|---|---|---|
| 25 | Phosphorous triethyl ester | 53 |
| 26 | Phosphorous triisopropyl ester | 73 |
| 27 | Phosphorous tributyl ester | 50 |

EXAMPLES 28–31

Example 1 was repeated, except that 0.05 mole of phosphorous triisopropyl ester was used in place of phosphorous monoethyl ester and 0.05 mole of each of carboxylic acids shown in Table 7 was used in place of acetic acid. The results obtained were as set forth in Table 7.

Table 7

| Example | Carboxylic acid | Resulting anilide | Yield* (%) |
|---|---|---|---|
| 28 | n-Butyric acid | n-Butyranilide | 77 |
| 29 | Isobutyric acid | Isobutyranilide | 74 |
| 30 | Pivalic acid | Pivalanilide | 61 |
| 31 | Benzoic acid | Benzanilide | 79 |

*based on carboxylic acid

EXAMPLES 32–33

Example 1 was repeated, except that 0.05 mole of phosphorous triisopropyl ester was used in place of phosphorous monoethyl ester and 20 ml. of each of the tertiary amines shown in Table 8 was used in place of pyridine. The results obtained were as set forth in Table 8.

Table 8

| Example | Tertiary amine | Acetanilide yield (%) |
|---|---|---|
| 32 | 2-Methylpyridine | 83 |
| 33 | 2,6-Dimethylpyridine | 59 |

EXAMPLE 34

A mixture of 5.5 g. (0.05 mole) of phosphorous monoethyl ester and 13.5 g. (0.05 mole) of mercuric chloride was heated under reflux (at about 115° C.) for 1 hour in 20 ml. of pyridine, whereby the reaction mixture became turbid to form a phosphonium salt. To the reaction mixture containing the phosphoronium salt was added 4.65 g. (0.05 mole) of aniline, and heating was continued under reflux for 1 hour to activate the amino group of aniline. After completion of the activation reaction, the reaction mixture was incorporated with 3.3 g. (0.055 mole) of acetic acid and then reacted under reflux for 2 hours. The reaction liquid was concentrated and then dissolved in 40 ml. of methanol, and the resulting solution was neutralized under cooling with a concentrated aqueous ammonia solution and then poured into 200 ml. of acetone to precipitate an ammonium salt. The precipitated ammonium salt was separated by filtration, and the filtrate was concentrated. Subsequently, water was added to the residue to form a solid. This solid was sufficiently washed with water and then recrystallized from water to obtain 2.23 g. of acetanilide, yield 33% based on aniline.

EXAMPLES 35–42

Example 34 was repeated, except that 0.05 mole of each of the phosphorous esters shown in Table 9 was used in place of phosphorous monoethyl ester and 0.055 mole of each of carboxylic acids shown in Table 9 was used in place of acetic acid. The results obtained were as set forth in Table 9.

Table 9

| Example | Phosphorous ester | Carboxylic acid | Resulting anilide | Yield (%) |
|---|---|---|---|---|
| 35 | Phosphorous monoethyl ester | Trifluoroacetic acid | Trifluoacet-anilide | 28 |
| 36 | Phosphorous monophenyl ester | Acetic acid | Acetanilide | 96 |
| 37 | Phosphorous diethyl ester | Acetic acid | Acetanilide | 93 |
| 38 | Phosphorous diisopropyl ester | Acetic acid | Acetanilide | 95 |
| 39 | Phosphorous diisopropyl ester | Pivalic acid | Pivalanilide | 65 |
| 40 | Phosphorous diphenyl ester | Acetic acid | Acetanilide | 95 |
| 41 | Phosphorous triethyl ester | Acetic acid | Acetanilide | 62 |
| 42 | Phosphorous triisopropyl ester | Acetic acid | Acetanilide | 86 |

EXAMPLE 43

To the same reaction mixture containing the phosphonium salt as in Example 1 was added a mixture of 3.0 g. (0.05 mole) of acetic acid and 5.2 g. (0.056 mole) of aniline, and the resulting mixture was reacted under reflux for 2 hours. Thereafter, the same aftertreatment as in Example 1 was effected to obtain acetanilide, yield 90% based on acetic acid.

EXAMPLE 44

Example 34 was repeated, except that 0.05 mole of phosphorous diisopropyl ester was used in place of phosphorous monoethyl ester and 0.05 mole of N-methylaniline was used in place of aniline, to obtain N-methylacetanilide, yield 53% based on N-methylaniline.

EXAMPLE 45

Example 1 was repeated, except that 0.05 mole of ammonium salt of phosphorous monophenyl ester was used in place of phosphorous monoethyl ester and 0.055 mole of iodine was used in place of mercuric chloride, to obtain acetanilide, yield 61% based on acetic acid.

EXAMPLES 46–49

Example 1 was repeated, except that 0.05 mole of phosphorous diisopropyl ester was used in place of phosphorous monoethyl ester, 0.05 mole of each of carboxylic acids shown in Table 10 was used in place of acetic acid and 0.055 mole of iodine was used in place of mercuric chloride. The results obtained were as set forth in Table 10.

Table 10

| Example | Carboxylic acid | Resulting anilide | Yield* (%) |
|---|---|---|---|
| 46 | Acetic acid | Acetanilide | 65 |
| 47 | Propionic acid | Propionanilide | 75 |
| 48 | Isobutyric acid | Isobutyranilide | 81 |
| 49 | Pivalic acid | Pivalanilide | 58 |

*based on carboxylic acid

EXAMPLE 50

Example 45 was repeated, except that 0.05 mole of phosphorous triethyl ester was used in place of ammonium salt of phosphorous monophenyl ester, to obtain acetanilide, yield 51% based on acetic acid.

EXAMPLES 51–53

Example 34 as repeated, except that 0.05 mole of each of the phosphorous esters shown in Table 11 was used in place of phosphorous monoethyl ester and 0.055 mole of iodine was used in place of mercuric chloride. The results obtained were as set forth in Table 11.

Table 11

| Example | Phosphorus ester | Acetanilide yield (%) |
|---|---|---|
| 51 | Phosphorus monophenyl ester | 60 |
| 52 | Phosphorus diisopropyl ester | 90 |
| 53 | Phosphorus triethyl ester | 45 |

EXAMPLE 54

A mixture of 7.9 g. (0.05 mole) of phosphorous monophenyl ester and 13.5 g. (0.05 mole) of mercuric chloride was reacted under reflux for 1 hour in 40 ml. of pyridine. After cooling the reaction liquid to 45° C., 10.45 g. (0.05 mole) of glycine (hereinafter represented by "Z—Gly.OH"; Gly shows a glycine residue) having an amino group protected with a benzyloxycarbonyl group (hereinafter represented by "Z"), 6.97 g. (0.05 mole) of glycine ethyl ester hydrochloride (hereinafter represented by "Gly.OEt.HCl") and 40 ml. of pyridine were added to the reaction liquid, and the resulting mixture was reacted at 45° C. for 12 hours.

After the reaction, liberated mercury was removed, and the reaction liquid was concentrated. The residue was extracted with ethyl acetate, and the ethyl acetate layer was washed with 2N—HCl, an aqueous sodium bicarbonate solution and water in this order. After dehydrating the ethyl acetate layer with sodium sulfate, ethyl acetate was removed under reduced pressure, and the residue was treated with petroleum ether to obtain 2.95 g. of N-benzyloxycarbonyl glycylglycine ethyl ester (hereinafter represented by "Z—Gly.Gly.OEt"), yield 20% based on Z—Gly.OH.

EXAMPLES 55–57

Example 54 was repeated, except that 0.05 mole of each of the phosphorous esters shown in Table 12 was used in place of phosphorous monophenyl ester. The results obtained were as set forth in Table 12.

Table 12

| Example | Phosphorous ester | Z—Gly . Gly . OEt yield (%) (based on Z—Gly . OH) |
|---|---|---|
| 55 | Phosphorous diisopropyl ester | 18 |
| 56 | Phosphorous diphenyl ester | 95 |
| 57 | Phosphorous triisopropyl ester | 23 |

EXAMPLE 58

A mixture of 11.70 g. (0.05 mole) of phosphorous diphenyl ester and 13.5 g. (0.05 mole) of mercuric chloride was reluxed for 1 hour in 40 ml. of pyridine. To the reaction mixture were then added 10.45 g. (0.05 mole) of Z—Gly.OH and 20 ml. of pyridine, and the resulting mixture was heated at 45° C. for 1.5 hours. Subsequently, 6.97 g. (0.05 mole) of Gly.OEt.HCl and 20 ml. of pyridine were added, and the mixture was reacted at 45° C. for 12 hours. Thereafter, the same after-treatment as in Example 54 was effected to obtain Z—Gly.-Gly.OEt in a yield of 84% based on Z—Gly.OH.

EXAMPLE 59

A mixture of 11.70 g. (0.05 mole) of phosphorous diphenyl ester and 13.5 g. (0.05 mole) of mercuric chloride was refluxed for 1 hour in 40 ml. of pyridine. To the reaction mixture were then added 6.97 g. (0.05 mole) of Gly.OEt.HCl and 20 ml. of pyridine, and the resulting mixture was heated at 45° C. for 1.5 hours. Subsequently, 10.45 g. (0.05 mole) of Z—Gly.OH and 20 ml. of pyridine were added, and the mixture was reacted at 45° C. for 12 hours. Thereafter, the same after-treatment as in Example 54 was effected to obtain Z—Gly.-Gly.OEt in a yield of 92% based on Z—Gly.OH.

EXAMPLE 60

Example 59 was repeated, except that 0.05 mole of mercurous chloride was used in place of mercuric chloride and the reaction after addition of the Z—Gly.OH was effected for 6 hours, to obtain Z—Gly.Gly.OEt in a yield of 92%.

EXAMPLE 61

Example 60 was repeated, except that 0.05 mole of glycylglycine ethyl ester hydrochloride (hereinafter represented by "Gly.Gly.OEt.HCl") was used in place of Gly.OEt.HCl, to obtain N-benzyloxycarbonyl glycylglycylglycine ethyl ester (hereinafter represented by "Z—Gly.Gly.Gly.OEt") in a yield of 82%.

EXAMPLE 62

Example 60 was repeated, except that 0.05 mole of N-benzyloxycarbonyl phenylalanine (hereinafter represented by "Z—Phe.OH") was used in place of Z—Gly.OH, to obtain N-benzyloxycarbonyl phenylalanyl glycine ethyl ester (hereinafter represented by "Z—Phe.Gly.OEt") in a yield of 80% based on Z—Phe.OH.

EXAMPLE 63

Example 62 was repeated, except that the reaction after addition of Z—Phe.OH was effected for 12 hours, to obtain Z—Phe.Gly.OEt in a yield of 91%, $[\alpha]_D$ −17.7 (C = 5, ethanol).

EXAMPLE 64

Example 63 was repeated, except that 0.05 mole of mercuric chloride was used in place of mercurous chloride, to obtain Z—Phe.Gly.OEt in a yield of 90%, $[\alpha]_D$ −17.6 (C = 5, ethanol).

EXAMPLE 65

Example 60 was repeated, except that 0.05 mole of tyrosine ethyl ester hydrochloride (hereinafter represented by "Tyr.OEt.HCl") was used in place of Gly.OEt.HCl, to obtain N-benzyloxycarbonyl glycyltyrosine ethyl ester (hereinafter represented by "Z—Gly.Tyr.OEt") in a yield of 78%.

EXAMPLE 66

Example 65 was repeated, except that the reaction after addition of Z—Gly.OH was effected for 12 hours, to obtain Z—Gly.Tyr.OEt in a yield of 91% $[\alpha]_D$ +19.8 (C = 5, ethanol).

EXAMPLE 67

Example 60 was repeated, except that 0.05 mole of N-benzyloxycarbonyl-α-glutamic acid (hereinafter represented by "Z—α—Glu.OH") in place of Z—Gly.OH, to obtain N-benzyloxycarbonyl-α-glutamylglycine ethyl ester (hereinafter represented by "Z—α—Glu.-Gly.OEt") in a yield of 72%.

EXAMPLE 68

A mixture of 2.93 g. (0.0125 mole) of phosphorous diphenyl ester and 3.40 g. (0.0125 mole) of mercuric chloride was refluxed for 1 hour in 20 ml. of pyridine. To the reaction mixture were then added 2.61 g. (0.0125 mole) of Z—Gly.OH and 10 ml. of pyridine, and the mixture was heated at 70° C. for 30 minutes. Subsequently, 0.94 g. (0.0125 mole) of Gly.OH and 20 ml. of pyridine were added, and the mixture was heated at 70° C. for 3 hours. Thereafter, liberated mercury was removed, and the reaction liquid was concentrated. The residue was extracted with ethyl acetate, and the ethyl acetate layer was washed with 2N—HCl and water in this order. After dehydrating the ethyl acetate layer with sodium sulfate, ethyl acetate was removed under reduced pressure, whereby a precipitate was formed. This precipitate was recrystallized from water to obtain Z—Gly.Gly.OH in a yield of 50% (1.7 g.).

EXAMPLE 69

Example 68 was repeated, except that 0.0125 mole of DL-alanine (hereinafter represented by "DL—Ala-.OH") was used in place of Gly.OH, to obtain Z—Gly.Ala.OH (DL) in a yield of 77%.

EXAMPLE 70

Example 68 was repeated, except that 0.0125 mole of L-leucine (hereinafter represented by "L—Leu.OH") was used in place of Gly.OH, to obtain Z—Gly.-Leu.OH (L) in a yield of 75%.

EXAMPLE 71

A mixture of 11.70 g. (0.05 mole) of phosphorous diphenyl ester and 8.8 g. (0.055 mole) of bromine was reacted at room temperature for 1 hour in 40 ml. of pyridine. To the reaction mixture were then added 10.45 g. (0.05 mole) of Z—Gly.OH, 6.97 g. (0.05 mole) of Gly.OEt.HCl and 40 ml. of pyridine, and the mixture was reacted at 45° C. for 12 hours. The reaction product was extracted with ethyl acetate, and thereafter the same operation as in Example 54 was conducted to obtain Z—Gly.Gly.OEt in a yield of 85%.

EXAMPLE 72

A mixture of 83 g. (0.05 mole) of phosphorous diisopropyl ester and 13.5 g. (0.05 mole) of mercuric chloride was heated under reflux (at about 115° C.) for 1 hour in 30 ml. of pyridine, whereby the reaction mixture became turbid to form a phosphonium salt. To the reaction mixture containing the phosphonium salt was added 4.4 g. (0.05 mole) of butyric acid, and heating was further continued under reflux for 1 hour to activate the carboxyl group of n-butyric acid. After completion of the activation reaction, the reaction mixture was incorporated with 4.1 g. (0.055 mole) of n-butanol and then reacted under reflux for 1 hour. Thereafter, the reaction liquid was subjected to fractional distillation to obtain 5.3 g. of butyl n-butyrate ester, yield 74% based on n-butyric acid.

EXAMPLES 73-74

Example 72 was repeated, except that 0.05 mole of each of the phosphorous ester derivatives shown in Table 13 was used in place of phosphorous diisopropyl ester. The results obtained were as set forth in Table 13.

Table 13

| Example | Carboxyl group-containing compound | Hydroxyl group-containing compound | Phosphorous ester derivative | Resulting ester | Yield (%) (based on n-butyric acid) |
|---|---|---|---|---|---|
| 73 | n-C$_3$H$_7$.COOH | n-C$_4$H$_9$OH | H$_2$RPO$_3$ (R=C$_6$H$_5$ ammonium salt) | n-C$_3$H$_7$.COOC$_4$H$_9$ | 78 |
| 74 | " | " | R$_3$PO$_3$ (R=C$_2$H$_5$) | " | 31 |

EXAMPLE 75

A mixture of 8.3 g. (0.05 mole) of phosphorous diisopropyl ester and 13.5 g. (0.05 mole) of mercuric chloride was heated under reflux for 1 hour in 40 ml. of pyridine, whereby the reaction mixture became turbid to form a phosphonium salt. To the reaction mixture containing the phosphonium salt was added 3.7 g. (0.05 mole) of n-butanol, and heating was further continued for 1 hour to activate the hydroxyl group of n-butanol. After completion of the activation reaction, the reaction mixture was incorporated with 4.8 g. (0.055 mole) of n-butyric acid and then reacted under reflux for 1 hour. Subsequently, the reaction liquid was cooled and extracted with ether, and the ether solution was fractionated to obtain 5.35 g. of butyl n-butyrate ester as a fraction of b.p. 75°-76° C./31 mmHg, yield 76% based on n-butanol.

EXAMPLES 76-77

Example 75 was repeated, except that 0.05 mole of each of the phosphorous ester derivatives shown in Table 14 was used in place of phosphorous diisopropyl ester. The results obtained were as set forth in Table 14.

Table 14

| Ex. | Hydroxyl group-containing compound | Carboxyl group-containing compound | Phosphorous ester derivative | Resulting ester | Yield (%) |
|---|---|---|---|---|---|
| 76 | n-C$_4$H$_9$OH | n-C$_3$H$_7$COOH | H$_2$RPO$_3$ (R=C$_6$H$_5$ ammonium salt) | n-C$_4$H$_9$.COO.C$_3$H$_7$ | 88 |
| 77 | " | " | R$_3$PO$_3$ (R=C$_2$H$_5$) | | 40 |

EXAMPLE 78

A mixture of 2.93 g. (0.0125 mole) of phosphorous diphenyl ester and 3.37 g. (0.0125 mole) of mercuric chloride was refluxed for 1 hour in 20 ml. of pyridine. Thereafter, 1.74 g. (0.0125 mole) of p-nitrophenyl and 10 ml. of pyridine were added, and the mixture was further reacted for 1 hour. To the reaction mixture were added 2.61 g. (0.0125 mole) of Z—Gly.OH having an amino group protected with Z and 10 ml. of pyridine, and the mixture was reacted under reflux for 1 hour. After completion of the reaction, pyridine was removed by distillation under reduced pressure, and the residue was extracted with 100 ml. of ethyl acetate. The ethyl acetate layer was washed with 2N—HCl, a saturated aqueous NaHCO$_3$ solution and water in this order and then dried over anhydrous Na$_2$SO$_4$, and thereafter ethyl acetate was removed by distillation under reduced pressure. The resulting residue was allowed to stand to form a solid, which was then recrystallized from ethanol to obtain N-benzyloxycarbonyl glycine p-nitrophenyl ester (hereinafter represented by

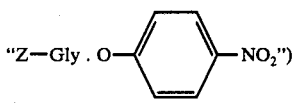

in a yield of 75% (3.0 g.).

EXAMPLE 79

β-Naphthol and Z—Gly.OH were treated in the same manner as in Example 78 to obtain N-benzyloxycarbonyl glycine β-naphthyl ester (hereinafter represented by

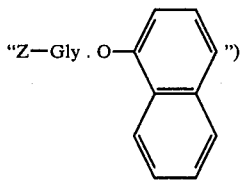

in a yield of 72%.

EXAMPLE 80 p-Hydroxybenzoic methyl ester and Z—Gly.OH were treated in the same manner as in Example 78 to obtain N-benzyloxycarbonyl glycine p-methoxycarbonylphenyl ester (hereinafter represented by

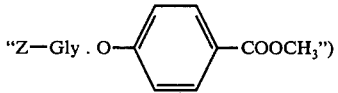

in a yield of 70%.

EXAMPLE 81

Using thiophenol and Z—Gly.OH, Example 78 was repeated, except that dichloromethane was used in place of ethyl acetate as the extraction solvent, to obtain N-benzyloxycarbonyl glycine phenylthio ester (hereinafter represented by

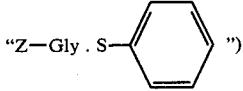

in a yield of 69%.

EXAMPLE 82

A mixture of 0.0125 mole of phosphorous diphenyl ester and 0.0125 mole of mercuric chloride was refluxed for 1 hour in 20 ml. of pyridine. To the reaction mixture were added 0.0125 mole of Z—Gly.OH and 0.0125 mole of p-nitrophenol simultaneously with 20 ml. of pyridine, and the mixture was reacted under reflux for 2 hours. After completion of the reaction, the same after-treatment as in Example 78 was effected to obtain

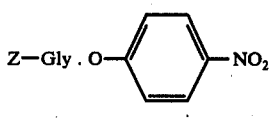

in a yield of 64%.

EXAMPLE 83

Example 82 was repeated, except that the mixture after addition of Z—Gly.OH and p-nitrophenol simultaneously with 20 ml. of pyridine was reacted at 45° C. for 20 hours, to obtain

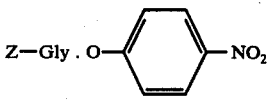

in a yield of 85%.

EXAMPLE 84

Example 83 was repeated, except that 0.0125 mole of mercurous chloride was used in place of mercuric chloride as the oxidizing agent, to obtain

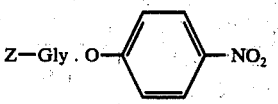

in a yield of 82%.

EXAMPLE 85

Example 83 was repeated, except that mercuric chloride as the oxidizing agent was used in an amount of 0.00625 mole, to obtain

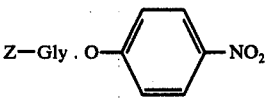

in a yield of 84%.

EXAMPLE 86

Example 83 was repeated, except that 0.0125 mole of phenylalanine (represented by "Z—Phe.OH") having an amino group protected with a benzyloxycarbonyl group was used in place of Z—Gly.OH, to obtain

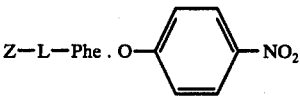

in a yield of 75%.

EXAMPLE 87

Example 83 was repeated, except that 0.0125 mole of bromine was used in place of mercuric chloride as the oxidizing agent to obtain

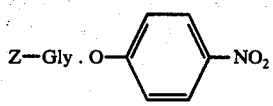

in a yield of 52%.

What is claimed is:

1. A process for producing an active ester of an amino acid having a protected amino group which comprises reacting the carboxyl group of an amino acid of the formula,

having a protected amino group, wherein $R^5$ is alkylene or alkylidene having 1–30 carbon atoms which may have a substituent selected from the group consisting of phenyl, salicyl, canbamoyl and carboxyl cycloalkylene or cycloalkylidene having 3–8 carbon atoms, phenylene, a group of the formula

a group of the formula

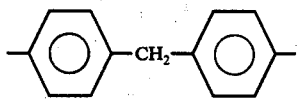

or a group in which two or more groups selected from the group consisting of the above-mentioned aliphatic and aromatic hydrocarbon groups are bonded through —CONH—; and $R^6$ is hydrogen or alkyl having 1–4 carbon atoms, with a phosphonium salt obtained by reacting a phosphorous ester selected from the group consisting of monomethyl, monoethyl, monoisopropyl, monophenyl, dimethyl, diethyl, diisopropyl, di-n-butyl, diphenyl, triethyl, triisopropyl and tributyl esters of phosphorous acid and an ammonium salt of the phosphorous monoester, with an organic base selected from the group consisting of pyridine, 2-methylpyridine, 3-methylpyridine, 4-methylpyridine, 2,6-dimethylpyridine or triethylamine, and an oxidizing agent selected from the group consisting of bromine, iodine, mercurous chloride, mercuric chloride, mercuric bromide or mercuric acetate, at a temperature of from 30° to 200° C., and then reacting the activated amino acid with a hydroxyl or mercapto group-containing compound of the formula

 (III-a)

or

 (III-b)

wherein $R^4$ is alkyl having 1–18 carbon atoms, cycloalkyl having 3–8 carbon atoms, phenyl, naphthyl, aryl having at least one substituent selected from the group consisting of alkyl having 1-4 carbon atoms, nitro, cyano, N,N-dimethylamino and methoxycarbonyl, or phenylalkyl having 7-12 carbon atoms, at a temperature of from 0° to 200° C.

2. A process according to claim 1, wherein the organic base is pyridine.

3. A process for producing an active ester of an amino acid having a protected amino group which comprises reacting the hydroxyl or mercapto group of a hydroxyl or mercapto group-containing compound of the formula $$R^4OH \qquad \text{(III-a)}$$

or $$R^4SH \qquad \text{(III-b)}$$

wherein $R^4$ is alkyl having 1-18 carbon atoms, cycloalkyl having 3-8 carbon atoms, phenyl, naphthyl, aryl having at least one substituent selected from the group consisting of alkyl having 1-4 carbon atoms, nitro, cyano, N,N-dimethylamino and methoxycarbonyl, or phenylalkyl having 7-12 carbon atoms, with a phosphonium salt obtained by reacting a phosphorus ester selected from the group consisting of monomethyl, monoethyl, monoisopropyl, monophenyl, dimethyl, diethyl, diisopropyl, di-n-butyl, diphenyl, triethyl, triisopropyl and tributyl esters of phosphorous acid, and an ammonium salt of the phosphorous monoester, with an organic base selected from the group consisting of pyridine, 2-methylpyridine, 3-methylpyridine, 4-methylpyridine, 2,6-dimethylpyridine or triethylamine, and an oxidizing agent selected from the group consisting of bromine, iodine, mercurous chloride, mercuric chloride, mercuric bromide or mercuric acetate, at a temperature of from 30° to 200° C., and then reacting the activated hydroxyl or mercapto group-containing compound with an amino acid of the formula

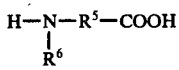

having a protected amino group, wherein $R^5$ is alkylene or alkylidene having 1-30 carbon atoms which may have a substituent selected from the group consisting of phenyl, salicyl, carbamoyl and carboxyl cycloalkylene or cycloalkylidene having 3-8 carbon atoms, phenylene, a group of the formula

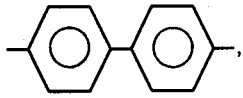

a group of the formula

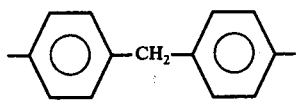

or a group in which two or more groups selected from the group consisting of the above-mentioned aliphatic and aromatic hydrocarbon groups are bonded through —CONH—; and $R^6$ is hydrogen or alkyl having 1-4 carbon atoms at a temperature of from 0° to 200° C.

4. A process according to claim 3, wherein the organic base is pyridine.

* * * * *